(12) United States Patent
Hiyama et al.

(10) Patent No.: US 8,999,443 B2
(45) Date of Patent: Apr. 7, 2015

(54) METHOD FOR FABRICATING A MICROARRAY OF SOFT MATERIALS

(75) Inventors: Satoshi Hiyama, Chiyoda-ku (JP); Kaori Kuribayashi, Bunkyo-ku (JP); Hiroaki Onoe, Bunkyo-ku (JP); Shoji Takeuchi, Bunkyo-ku (JP)

(73) Assignees: NTT DOCOMO, INC., Tokyo (JP); The University of Tokyo, Tokyo (JP)

( * ) Notice: Subject to any disclaimer, the term of this patent is extended or adjusted under 35 U.S.C. 154(b) by 0 days.

(21) Appl. No.: 13/814,588

(22) PCT Filed: Mar. 27, 2012

(86) PCT No.: PCT/JP2012/057996
§ 371 (c)(1),
(2), (4) Date: Feb. 6, 2013

(87) PCT Pub. No.: WO2012/133450
PCT Pub. Date: Oct. 4, 2012

(65) Prior Publication Data
US 2013/0136863 A1 May 30, 2013

(30) Foreign Application Priority Data
Mar. 28, 2011 (JP) ................. 2011-070934

(51) Int. Cl.
*C23C 16/00* (2006.01)
*B05D 1/32* (2006.01)
(Continued)

(52) U.S. Cl.
CPC ............... *B05D 1/325* (2013.01); *C12N 15/09* (2013.01); *G01N 37/00* (2013.01); *G01N 33/543* (2013.01);
(Continued)

(58) Field of Classification Search
CPC ........ B05D 1/325; C23C 14/12; C23C 16/56; C23C 14/5873; B32B 33/00; C12N 15/09; G01N 33/543; G01N 37/00
USPC .................. 427/2.1, 2.11, 255.6, 255.7, 259
See application file for complete search history.

(56) References Cited

U.S. PATENT DOCUMENTS 6,559,474 B1 * 5/2003 Craighead et al. .............. 257/40

FOREIGN PATENT DOCUMENTS

JP 2006-114489 4/2006
JP 2008-014352 1/2008

OTHER PUBLICATIONS

Ilic, B. et al., "Topographical Patterning of Chemically Sensitive Biological Materials Using a Polymer-Based Dry Lift Off," Biomedical Microdevices, vol. 2, No. 4, pp. 317 to 322, (2000).
(Continued)

*Primary Examiner* — Elizabeth Burkhart
(74) *Attorney, Agent, or Firm* — Oblon, McClelland, Maier & Neustadt, L.L.P.

(57) ABSTRACT

A method for fabricating a microarray of plural soft materials includes: vapor-depositing a first layer poly(para-xylylene) resin on a substrate, forming a first micro pattern in the poly(para-xylylene) resin; obtaining a substrate including a first microarray formed by pouring a first soft material solution, freeze-drying the first soft material to obtain a micro-arrayed substrate of the freeze-dried first soft material; vapor-depositing a second layer poly(para-xylylene) resin on the micro-arrayed substrate of the freeze-dried first soft material, forming a second micro pattern placed differently from the first micro pattern by penetrating the poly(para-xylylene) resin of the first and second layers, forming a second microarray on the substrate by pouring a second soft material solution; and forming a microarray of the first and second soft materials on the substrate by peeling off the poly(para-xylylene) resin of the first and second layers.

12 Claims, 6 Drawing Sheets (51) Int. Cl.
 C12N 15/09 (2006.01)
 G01N 37/00 (2006.01)
 G01N 33/543 (2006.01)
 B81C 1/00 (2006.01)

(52) U.S. Cl.
 CPC .... B81C 1/00206 (2013.01); *B01J 2219/00317* (2013.01); *B01J 2219/00529* (2013.01); *B01J 2219/00637* (2013.01); *B01J 2219/00659* (2013.01); *B01J 2219/00722* (2013.01); *B01J 2219/00725* (2013.01); *B81B 2201/0214* (2013.01); *B81B 2201/058* (2013.01)

(56) References Cited

OTHER PUBLICATIONS

Tan, C. et al., "Nanoscale Resolution, Multicomponent Biomolecular Arrays Generated by Aligned Printing With Parylene Peel-Off," Nano Letters, vol. 10, pp. 719 to 725, (2010).

Kuribayashi, K. et al., "Sequential Parylene Lift-Off Process for Selective Patterning of Biological Materials," IEEE MEMS, pp. 501 to 504, (Jan. 2007).

Atsuta, K. et al., "A parylene lift-off process with microfluidic channels for selective protein patterning," Journal of Micromechanics and Microengineering, vol. 17, pp. 496 to 500, (2007).

Hiyama, S. et al., "Biomolecular-motor-based autonomous delivery of lipid vesicles as nano- or microscale reactors on a chip," Lab on a Chip, vol. 10, pp. 2741 to 2748, (2010).

Hsiao, S. et al., "Direct Cell Surface Modification with DNA for the Capture of Primary Cells and the Investigation of Myotube Formation on Defined Patterns," Langmuir Article, vol. 25, No. 12, pp. 6985 to 6991, (2009).

Stamou, D. et al., "Self-Assembled Microarrays of Attoliter Molecular Vessels," Angewandte Chemie International Edition, vol. 42, pp. 5580 to 5583, (2003).

Ito, A. et al., "Magnetite nanoparticle-loaded anti-HER2 immunoliposomes for combination of antibody therapy with hyperthermia," Cancer Letters, vol. 212, pp. 167 to 175, (2004).

International Search Report Issued Jun. 26, 2012 in PCT/JP12/57996 Filed Mar. 27, 2012.

Japanese Office Action mailed Apr. 8, 2014 in Japanese patent application No. 2011-070934 with English Translation.

Satoshi Hiyama, et al., "Micropatterning of Different Kinds of Biomaterials as a Platform of a Molecular Communication System", Computer Communications Workshops (Infocom Wkshps), 2011 IEEE Conference on, IEEE, Apr. 10, 2011, pp. 479-484.

Supplementary European Search Report issued Jul. 16, 2014 in application European Application No. 12763427.

* cited by examiner

FIG.2B (i) VAPOR-DEPOSIT POLY (PARA-XYLYLENE) RESIN OF SECOND LAYER (j) SPIN COAT PHOTORESIST (k) PHOTOLITHOGRAPHY (l) DEVELOP (m) DRY ETCHING BY OXYGEN PLASMA (n) WASH

(o) INJECT SECOND SOFT MATERIAL

(o') DISMANTLE FLOW CELL

(p) PEEL OFF POLY (PARA-XYLYLENE) RESIN OF FIRST AND SECOND LAYERS (q) INJECT BUFFER SOLUTION

FIG.3

METHOD FOR FABRICATING A MICROARRAY OF SOFT MATERIALS

TECHNICAL FIELD

The present invention relates to a method for fabricating a microarray of soft materials. More particularly, the present invention relates to a method for fabricating a microarray of plural kinds of soft materials on a same substrate.

BACKGROUND ART

In recent years, in the field of medical care and diagnosis or in the field of research in molecular and cellular biology, methods and apparatuses are being required for measuring and observing analysis, functional evaluation or interactive analysis for proteins, DNAs(deoxyribo nucleic acids) or cells, more quantitatively, with good repeatability and quickly. As one field of such techniques, various techniques are proposed for fabricating a soft material array on a substrate such as a glass on a scale of micrometers to nanometers. The "soft materials" may be biological materials or non-biological materials. The "soft materials" widely mean macromolecules in which small molecules are connected (or collected) in various forms, gel, gum, colloid, micelle, liquid crystal, and various biological macromolecules (nucleic acids such as DNAs and RNAs, proteins, carbohydrates, glycoproteins, and the like).

One of the techniques, a method is gathering attention for fabricating a microarray of a soft material by patterning a poly(para-xylylene) resin to produce a stencil. In the non-patent document 1, a method is disclosed for fabricating a microarray of a soft material on a substrate (so-called poly(para-xylylene) resin lift-off method), wherein the method includes: forming a micro pattern in a poly(para-xylylene) resin that is vacuum-deposited on a substrate to produce a stencil; pouring a soft material onto the stencil; and after that, peeling the poly(para-xylylene) resin from the substrate to fabricate the microarray. However, although the non-patent document 1 discloses a technique for forming one kind of soft material into a microarray with versatility and with scalability, the non-patent document 1 does not disclose a technique for making arrays on the same substrate using a plurality of different kinds of soft materials.

On the other hand, several techniques that use the poly(para-xylylene) resin are known for forming plural kinds of soft materials into a microarray on a substrate.

For example, the non-patent document 2 discloses a technique that includes: forming a micro pattern in a poly(para-xylylene) resin that is vacuum-deposited on a substrate to produce a stencil; discharging plural kinds of soft materials on the stencil using an inkjet printing scheme; peeling off the poly(para-xylylene) resin from the substrate so as to fabricate a microarray of plural kinds of soft materials on the same substrate. However, this technique has a problem in that, not only a high-performance spotter that can discharge soft materials becomes necessary as an additional special apparatus, but also spot intervals depend on the performance of the spotter. That is, there is a problem in that spot intervals for forming an array from different kinds of soft materials are limited in order to avoid contamination (unintentional mixture) among the different kinds of soft materials, depending on the performance of the spotter.

Also, the non-patent document 3 discloses a technique that includes: forming a micro pattern in two layers of poly(para-xylylene) resin that are vacuum-deposited on a substrate to produce a stencil; peeling off the two layers of the poly(para-xylylene) resin sequentially from the substrate after pouring soft materials onto the stencil so as to fabricate a microarray of plural kinds of soft materials on the same substrate. However, in this technique, there is a problem in that a possibility that contamination may occur among different kinds of soft materials cannot be excluded.

Further, the non-patent document 4 discloses a technique that includes: forming a micro pattern in one layer of poly(para-xylylene) resin that is vacuum-deposited on a substrate to produce a stencil; forming a plurality of micro flow channels on the stencil; peeling off the poly(para-xylylene) resin from the substrate after injecting different kinds of soft materials into each flow channel so as to form a microarray of plural kinds of soft materials on the same substrate. In this technique, although the possibility of occurrence of contamination is small, since a micro flow channel is connected to each spot of the microarray, there is a problem in that the spot interval for forming the array from the different kinds of soft materials cannot become a desirable size and that it is difficult to fabricate an array of a large area.

PRIOR ART DOCUMENTS

[Non-patent document 1] B. Ilic, et al., "Topographical Patterning of Chemically Sensitive Biological Materials Using a Polymer-Based Dry Lift Off," Biomedical Microdevices, vol. 2, pp. 317-322, 2000.

[Non-patent document 2] C. P. Tan, et al., "Nanoscale Resolution, Multicomponent Biomolecular Arrays Generated by Aligned Printing with Parylene Peel-Off," Nano Letters, vol. 10, pp. 719-725, 2010.

[Non-patent document 3] K. Kuribayashi, et al., "Sequential Parylene Lift-Off Process for Selective Patterning of Biological Materials," Proc. IEEE MEMS'07, pp. 501-504, 2007.

[Non-patent document 4] K. Atsuta, et al., "A Parylene Lift-Off Process with Microfluidic Channels for Selective Protein Patterning," Journal of Micromechanics and Microengineering, vol. 17, pp. 496-500, 2007.

SUMMARY OF THE INVENTION

Problem to be Solved by the Invention

An object of the present invention is to provide a method for fabricating a microarray of small intervals of soft materials using the poly(para-xylylene) resin lift-off method, wherein the method is for fabricating a microarray of plural kinds of soft materials on a same substrate with versatility and with scalability, without contamination among the plural soft materials.

Means for Solving the Problem

The inventors of the present invention pursued a method for forming plural kinds of soft materials into a microarray on the same substrate. As a result, the inventors have found that, (i) by dehydrating (freeze-drying and the like, for example) a soft material on a substrate (that is obtained by the poly(para-xylylene) resin lift-off method, for example) without denaturation, a normal poly(para-xylylene) resin lift-off method can be applied to the substrate, and further (ii) the poly(para-xylylene) resin laminated on the soft material can be smoothly peeled off from the substrate without impairment of fixing state, structure and function of the soft material, so that the inventors have completed the present invention.

That is, the present invention is a method for fabricating a microarray of plural kinds of soft materials, including:

vapor-depositing a poly(para-xylylene) resin of a first layer on a substrate;

forming a first micro pattern in the poly(para-xylylene) resin;

forming a first microarray on a surface of the substrate by pouring a solution of a first soft material;

freeze-drying the first soft material so as to form a micro-arrayed substrate of the first soft material;

vapor-depositing and laminating a poly(para-xylylene) resin of a second layer on the micro-arrayed substrate of the first soft material;

forming a second micro pattern in a place different from the first micro pattern on the micro-arrayed substrate of the first soft material by penetrating the poly(para-xylylene) resin of the first layer and the second layer;

forming a second microarray on a surface of the substrate by pouring a solution of a second soft material;

peeling off the poly(para-xylylene) resin of the first layer and the second layer at the same time so as to form a micro-arrayed substrate of the first and the second soft materials; and dissolving the first soft material by pouring a buffer solution to the micro-arrayed substrate of the first and the second soft materials, or freeze-drying the second soft material, so as to fabricate a microarray of the first and the second soft materials on the same substrate.

Further, by repeating the method of the present invention, a microarray of desirable kinds of different soft materials is fabricated.

Effect of the Present Invention

According to the present invention, by using the poly(para-xylylene) resin lift-off method, a microarray of small intervals can be fabricated on the same substrate without contamination of plural kinds of soft materials, for versatile purposes, with scalability, without using a spotter. Also, by repeating the microarray fabrication method of the present invention, not only the microarray of the two kinds of soft materials, but also a microarray of more than two kinds of soft materials can be fabricated. Further, the microarrayed substrate on which a freeze-dried soft material is fixed can be preserved for a long time and can be delivered at room temperature or at low temperature. Thus, a user can easily use the microarrayed substrate only by pouring a buffer solution when the user uses the substrate.

EMBODIMENTS FOR CARRYING OUT THE INVENTION

In the following, preferred embodiments of the present invention are described with reference to figures. But, the present invention is not limited to these embodiments.

Figure 1:
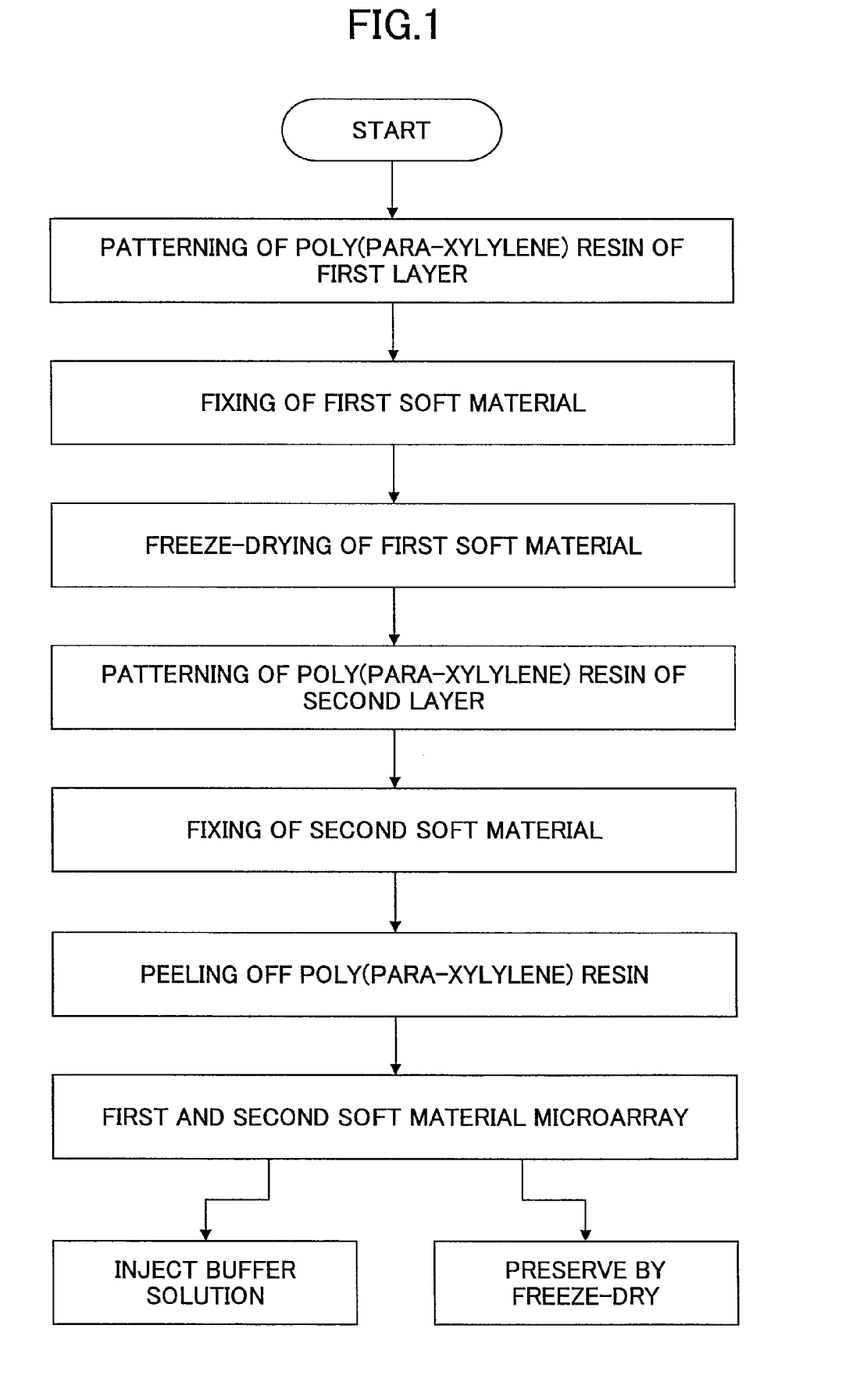
FIG. 1 is a conceptual diagram showing a method for fabricating a microarray of soft materials as an embodiment of the present invention.

FIG. 1 is a diagram conceptually showing a method of an embodiment of the present invention. The method for fabricating a microarray of plural kinds of soft materials in an embodiment of the present invention utilizes the so-called conventional poly(para-xylylene) resin lift-off method, and includes the poly(para-xylylene) resin lift-off method known so far or various application methods of the poly(para-xylylene) resin lift-off method. In the method of the embodiment of the present invention, there is no limitation in conditions, materials, reaction conditions and the like for the normal poly(para-xylylene) resin lift-off method.

As shown in FIG. 1, the method of the embodiment of the present invention includes, first, a process of vapor-depositing a poly(para-xylylene) resin of a first layer onto a substrate, forming a first micro pattern in the poly(para-xylylene) resin of the first layer, and pouring a solution including a first soft material, so as to obtain a substrate on which a first microarray is formed (fixed). This process is a process for applying the conventional poly(para-xylylene) resin lift-off method, and the obtained substrate is one on which the first microarray is formed (fixed). In the embodiment of the present invention, there is no limitation in shapes of individual patterned microarrays, sizes of individual soft materials, and distances among individual soft materials, and the like (to be referred to as "shapes and the like" hereinafter). Shapes and the like that can be designed by the conventional poly(para-xylylene) resin lift-off method can be adopted. Normally, it is easy to design in a micrometer size or a nanometer size.

Usually, the poured first soft material is fixed on the substrate as a form of a water solution or a proper solution. Also, there is no limitation in the pouring method. The soft material is fixed on the surface of the substrate by pouring a water solution or a solution of a proper solvent of the first soft material on a part of or the whole of the substrate. After that, excessive water solution and the like of the soft material that is not fixed can be washed away. Any modification for accelerating bonding with the soft material is not necessary on the surface of the substrate, but, processing may be performed for strengthening bonding with the soft material according to circumstances.

The method of the embodiment of the present invention includes, next, a process of freeze-drying the obtained first soft material so as to obtain a substrate on which a microarray of the freeze-dried first soft material is formed. In the embodiment of the present invention, the first soft material fixed on the substrate is freeze-dried. In the embodiment of the present invention, "freeze-drying" widely means "removing water from the soft material on the substrate such that the structure and the function of the soft material are not irreversibly denatured". Therefore, presence or absence of cooling, presence or absence of freeze-cushion buffer such as sucrose or trehalose, presence or absence of vacuum operation can be properly selected according to the soft material to be freeze dried on the substrate. Also, "freeze-dry" may be performed on the whole or a part of the soft material on the substrate, or may be performed for the whole of the substrate.

Next, the method of the embodiment of the present invention includes a process of vapor-depositing again a poly(para-xylylene) resin of a second layer onto the obtained substrate on which the microarray of the first soft material is formed so as to form a second micro pattern in the poly(para-xylylene) resin of the second layer. In this process, the poly(para-xylylene) resin of the second layer is vapor-deposited onto the substrate including the surface of the first soft material that is fixed and freeze-dried on the substrate. The vapor-deposition coating can be performed under a normal condition of poly(para-xylylene) resin vapor-deposition coating. Also, as described below, by the vapor-deposition coating, any damage such as denaturation is not found not only on the surface of the first soft material but also in the inside. The reason is that the first soft material fixed on the substrate is sufficiently dried. Further, the normal condition of the poly(para-xylylene) resin lift-off method as described above can be also applied to forming of the second micro pattern in the poly(para-xylylene) resin of the second layer. To form the second micro pattern in the poly(para-xylylene) resin of the second layer is to provide a microarray of the first and the second soft materials on the same surface of the substrate. Thus, the second micro pattern is formed on a place of the substrate different from a place of the first micro pattern by penetrating the poly(para-xylylene) resin of the first layer and the second layer.

Further, the method of the embodiment of the present invention includes pouring a solution that includes the second soft material in the obtained second micro pattern of the poly(para-xylylene) resin of the second layer so as to form (fix) a second microarray on the substrate. This process may be the same as the above-mentioned method for pouring the solution including the first soft material.

In a case where fabrication of a microarray using two different kinds of the first and the second soft materials is intended, the microarray of the first and the second soft materials can be fabricated on the same surface of the substrate by peeling off the poly(para-xylylene) resin from the substrate on which the obtained second microarray is formed (fixed). The first soft material is in a state of dry, and the second soft material is in a state of a solution (wet).

As necessary, by freeze-drying again the whole substrate, the first and the second soft materials can be dried, or, by supplying a buffer solution and the like, the first and the second soft materials can be made in a wet state. By freeze-drying the whole substrate, the soft materials can be preserved at room temperature or at low temperature.

Although FIG. 1 shows the processes using consecutive arrows, in the present embodiment of the present invention, not only the above-described microarray of the first and the second soft materials, but also a microarray in which equal to or greater than three kinds of soft materials are formed on the surface of the same substrate can be fabricated by repeating the above-mentioned processes as necessary.

As described above, the target of vapor-deposition coating of the poly(para-xylylene) resin of the second layer is the substrate on which the first soft material is fixed and freeze-dried and the first layer of the poly(para-xylylene) resin is held. But, the embodiment of the present invention is not limited to this.

A resultant substrate that is obtained by, after pouring the first soft material and fixing it on the substrate, peeling off the first poly(para-xylylene) layer and freeze-drying also becomes the target, and also, a resultant substrate that is obtained by, after pouring the first soft material and fixing it on the substrate, freeze-drying, and after that, peeling off the first poly(para-xylylene) layer also becomes the target.

In the following, the embodiment of the present invention is described in more detail based on examples.

EXAMPLE

Method for Fabricating a Microarray

Figure 2A:
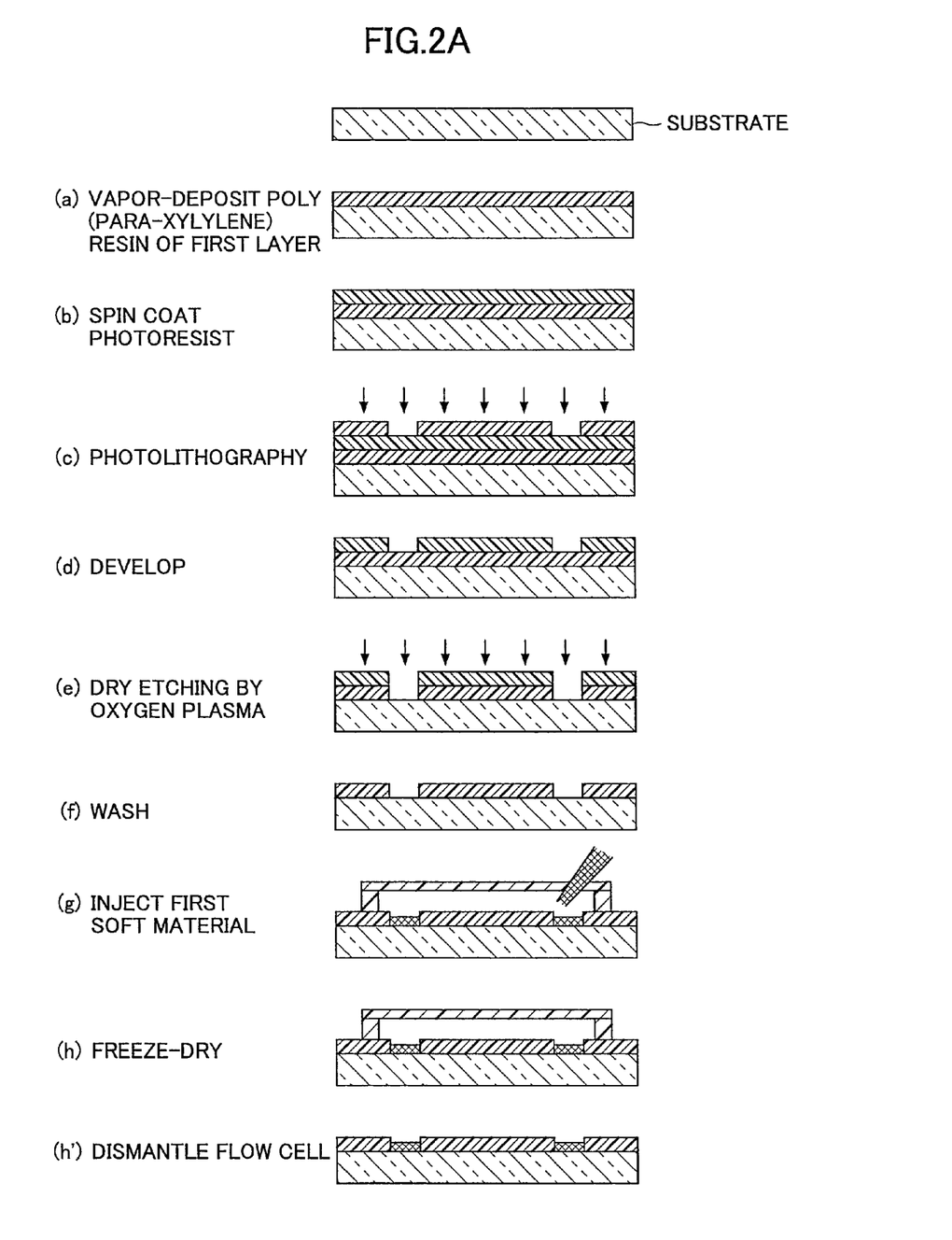
FIG. 2A is a diagram showing a detailed procedure of the method for fabricating the microarray of soft materials as an embodiment of the present invention.
Figure 2B:
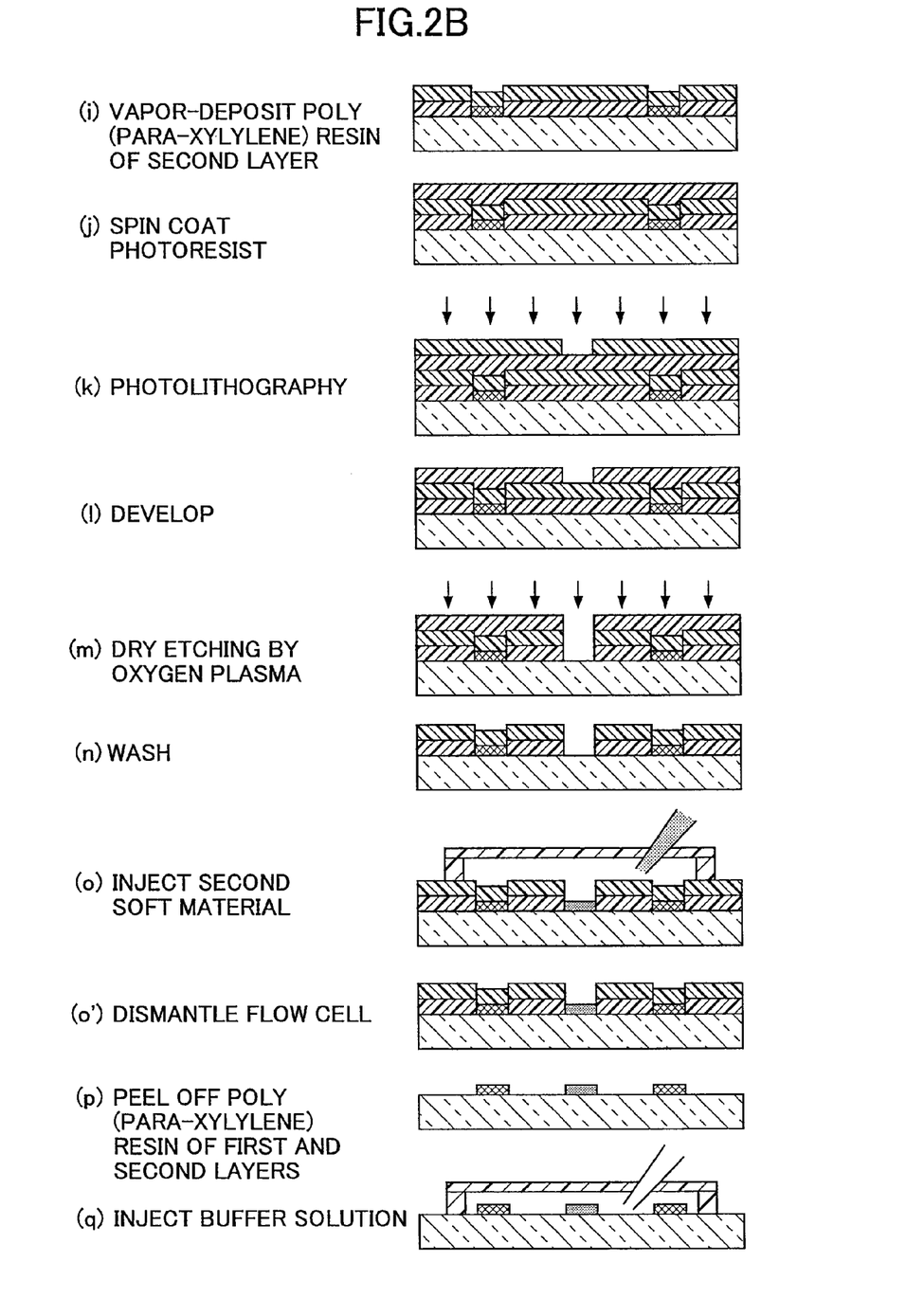
FIG. 2B is a diagram showing a detailed procedure of the method for fabricating the microarray of soft materials as an embodiment of the present invention.

FIGS. 2A and 2B show a procedure of the fabrication method of the example in detail. Description will be given with reference to FIGS. 2A and 2B.

First, the poly(para-xylylene) resin of the first layer is vacuum-evaporated onto the substrate (FIG. 2A(a)).

It is only necessary that the substrate is made of a material that can fix the soft material and that can tolerate poly(para-xylylene) vapor-deposition coating condition. For example, the material may be glass, silicon, plastic and the like. In a case where the microarray is used and where it is preferable that the substrate is light-permeable for the purpose of measurement and the like, it is preferable that the material is glass that is light-permeable. Also, although the method for fixing the soft material on the surface of the substrate is not limited to a specific method, it is possible to perform processing on the surface of the substrate for accelerating fixing.

Although the type of the poly(para-xylylene) resin to be vapor-deposited onto the substrate is not limited to a particular one, parylene C (Parylene Japan, Limited Liability Company) is used as an example in this description. Other kinds of parylene N, parylene D, parylene HT or the like can be properly selected as necessary (all of these can be purchased from Parylene Japan, Limited Liability Company). Vapor-deposition coating thickness of the poly(para-xylylene) resin is not limited to a particular value, and it is only necessary that, by the thickness, a pattern having a structure in which the soft material is sufficiently poured in the later process can be formed. More particularly, it is desirable that the thickness is equal to or less than 2 μm. Description is given in which the vapor-deposition coating is performed with a thickness of 1 μm, as an example.

Next, a photoresist is laminated on the vapor-deposited poly(para-xylylene) resin. In the following description, S1818 (Shipley Far East Ltd.) is used as a photoresist as an example, but the photoresist is not limited to this particular one. Also, there is no limitation for the laminating method. For example, a normal method such as a method of spin coating is preferable.

Photolithography is performed by irradiating ultraviolet light via a glass photo mask on which the first micro pattern is drawn (FIG. 2A(c)), and further, development of the photoresist is performed (FIG. 2A (d)). The developer can be selected depending on which photoresist is used with it. For example, when S1818 is used as the photoresist, NMD-3 (that can be purchased from TOKYO OHKA KOGYO CO., LTD.) can be used as a developer.

After that, dry etching by oxygen plasma is performed, so that the first micro pattern is drawn on the poly(para-xylylene) resin (FIG. 2A(e). Here, although photolithography by irradiation of ultraviolet light and dry etching by oxygen plasma are described as examples, the methods for photolithography and dry etching are not limited to these. For example, lithography using an electron beam may be adopted.

Next, the remaining photoresist is washed away by using acetone and isopropyl alcohol so as to form the first micro pattern on the glass substrate (FIG. 2A(f)).

Next, a flow cell is fabricated on the poly(para-xylylene) resin of the first layer in which the micro pattern has been formed in order to pour the first soft material (FIG. 2A (g)). In this example, the flow cell is fabricated by using a silicon rubber sheet as a spacer, for example, and sandwiching the silicon rubber sheet with cover glasses. A solution including the first soft material by which the microarray is to be fabricated is injected in the flow cell, so that the first microarray is introduced and formed on the exposed surface of the glass substrate. In this embodiment, biotinylated BSA (bovine serum albumin) of 4 mg/mL, streptavidin of 1 mg/mL, biotinylated single-stranded DNAs (23 base length, fluorochrome FITC (fluorescein isothiocyanate) modified) of 5 μM are laminated as the first soft material sequentially.

After pouring the first soft material, the solution in the flow cell is replaced with a solution that does not include salt, such as a ultrapure water or a distillated water, for example. Accordingly, the first soft material that remains in the flow cell or the first soft material that is isolated and is not fixed on the substrate is completely washed away.

After that, the whole substrate including the flow cell is freeze-dried using a freeze-drying apparatus (FIG. 2A(h)). Further, after the solution including the first soft material is completely dried, the flow cell is dismantled (FIG. 2A(h')). Or, after dismantling the flow cell, the whole substrate that does not include the flow cell may be freeze-dried.

Next, the poly(para-xylylene) resin of the second layer is vacuum-evaporated and laminated with a thickness of 1 μm, for example, on the substrate that is freeze-dried by using the condition and procedure similar to those of the first layer (FIG. 2B(i)). Next, a photoresist such as S1818 is laminated by spin coating (FIG. 2B(j)).

Baking condition of the photoresist may be high temperature and short time length (for example, one minute at 100° C.) in consideration of characteristics (thermosensitivity and the like, for example) of the freeze-dried first soft material, or may be low temperature and long time length (for example, three hours at 35° C.), or a condition obtained by combining them can be selected.

After that, photolithography is performed by irradiating ultraviolet light via a glass photo mask on which the second micro pattern is drawn (FIG. 2B(k)), and development of the photoresist is performed using NMD-3 (FIG. 2B(l)).

After that, dry etching by oxygen plasma is performed, so that the second micro pattern is drawn on a place different from the first micro pattern by penetrating the poly(para-xylylene) resin of the first layer and the second layer (FIG. 2B(m)). There is no limitation in the dry etching condition for penetrating the poly(para-xylylene) resin of the first layer and the second layer. The dry etching condition can be easily selected by adjusting etching time, for example, according to the thickness of the poly(para-xylylene) resin of the first layer and the second layer.

By washing away the remaining photoresist by using acetone and isopropyl alcohol, the second micro pattern is formed on the surface of the glass substrate (FIG. 2B(n)).

Next, a flow cell is fabricated on the poly(para-xylylene) resin of the second layer in which the micro pattern has been formed, under a condition similar to that of the first layer (FIG. 2B (o)).

Then, a solution including the second soft material by which the microarray is to be fabricated is injected in the flow cell, so that the second microarray is formed on the exposed surface of the glass substrate. In this embodiment, biotinylated BSA (bovine serum albumin) of 4 mg/mL, streptavidin of 1 mg/mL, biotinylated single-stranded DNAs (23 base length, fluorochrome TMR (tetramethyl rhodamine) modified) of 5 μM are laminated as the second soft material sequentially. In this example, since the place where pattering of the first soft material has been performed is covered by the poly(para-xylylene) resin of the second layer, contamination between the first soft material and the second soft material can be completely inhibited. After that, the flow cell is dismantled (FIG. 2B(o')).

Further, the poly(para-xylylene) resin of the first layer and the second layer are peeled off at the same time. The first layer and the second layer of the poly(para-xylylene) resin can be easily peeled off by peeling off a part of the layers using a pair of tweezers, for example.

Finally, a flow cell is fabricated on the substrate (FIG. 2B(q)), and a buffer solution is poured, so that the freeze-dried first soft material is re-dissolved and a microarray of the first and the second soft materials is fabricated.

[Evaluation of the Fabricated Microarray]

Figure 3:
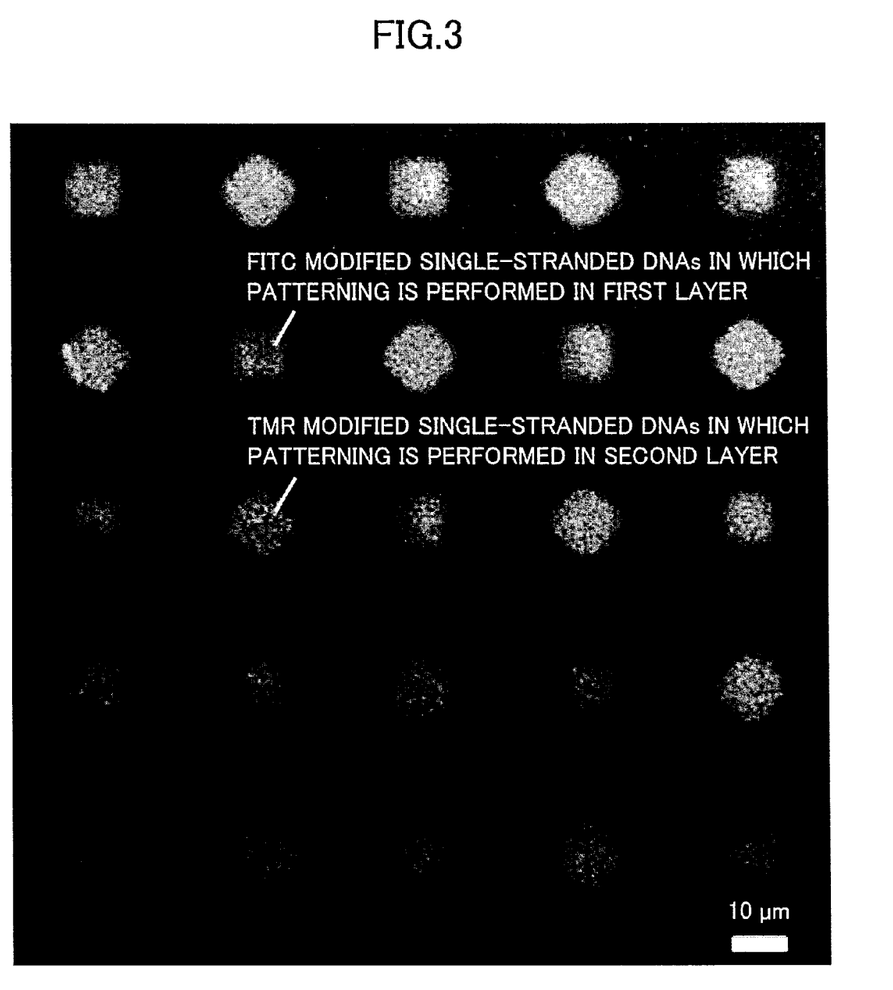
FIG. 3 is an observation image of a fluorescence microscope showing a result of fabricating a microarray of single-stranded DNAs having different base sequences and fluorochromes.

FIG. 3 shows an example of an observation result of a fluorescence microscope showing a microarray that is fabricated by the above-mentioned procedure. Following features are apparent from FIG. 3. (i) First, the two different kinds of soft materials are fixed on the glass substrate sufficiently against the following various processes. (ii) Further, the two different kinds of soft materials fulfill functions without denaturation, wherein each of the soft materials is a labeled protein constructed by combining plural functions of proteins. (iii) There is no contamination in the two different kinds of soft materials. That is, it is understood that the FITC modified single-stranded DNAs as the first soft material and the TMR modified single-stranded DNAs as the second soft material form a microarray on the same substrate without contamination. (iv) The array is formed in a micro scale, and the interval between spots that form the array is separated sufficiently clearly.

Although FIG. 3 shows an example intended to obtain an array of a micrometer scale by using conditions and an apparatus for obtaining an array of a micrometer scale, it is possible, if necessary, to obtain an array in a nanometer scale by using conditions and an apparatus intended for obtaining a normal array of a nanometer scale, for example, by performing lithography using an electron beam.

Figure 4:
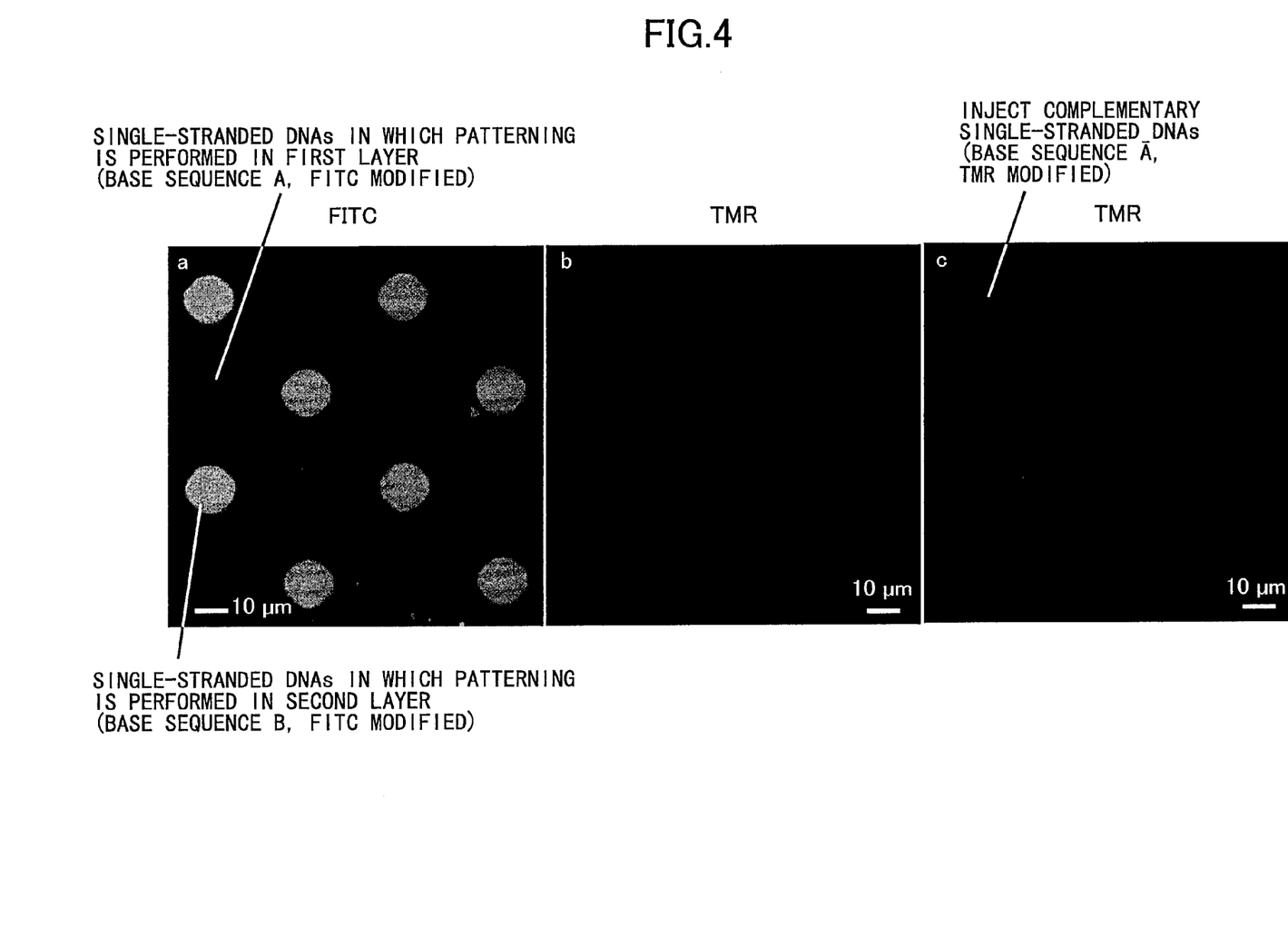
FIG. 4 is an observation image of a fluorescence microscope showing a result of verifying ability of hybridization of freeze-dried single-stranded DNAs.

FIG. 4 is an image of observation of a fluorescence microscope showing a result of an experiment for verifying whether the single-stranded DNAs (soft materials) by which the microarray are formed in the embodiment of the present invention has an ability of hybridization.

In this experiment, biotinylated BSA of 4 mg/mL, streptavidin of 1 mg/mL, biotinylated single-stranded DNAs (23 base length, fluorochrome FITC modified, base sequence A) of 5 μM were laminated as the first soft material sequentially. Also, biotinylated BSA of 4 mg/mL, streptavidin of 1 mg/mL, biotinylated single-stranded DNAs (23 base length, fluorochrome FITC modified, base sequence B) of 5 μM were laminated as the second soft material sequentially. It was verified that, the fabrication result of the microarray was observed via a fluorescent filter of FITC (FIG. 4a), but was not observed via a fluorescent filter of TMR (FIG. 4b).

From FIG. 4, it is verified that the micro-arrayed single-stranded DNAs formed via the process of freeze-drying by the method of the embodiment of the present invention keep their ability of hybridization, and it is understood that denaturation and the like is not received. That is, it is confirmed that, by pouring complementary strands (cholesterol modified single-stranded DNAs of 5 μM, 23 base length, fluorochrome TMR modified, base sequence A) of the single-stranded DNAs of base sequence A on which the process of freeze-drying has been performed, the complementary strands are specifically bonded only to a spot where the single-stranded DNAs of the base sequence A is fixed (FIG.

4c), and the single-stranded DNAs on which the process of freeze-drying has been performed has the ability of hybridization.

Figure 5:
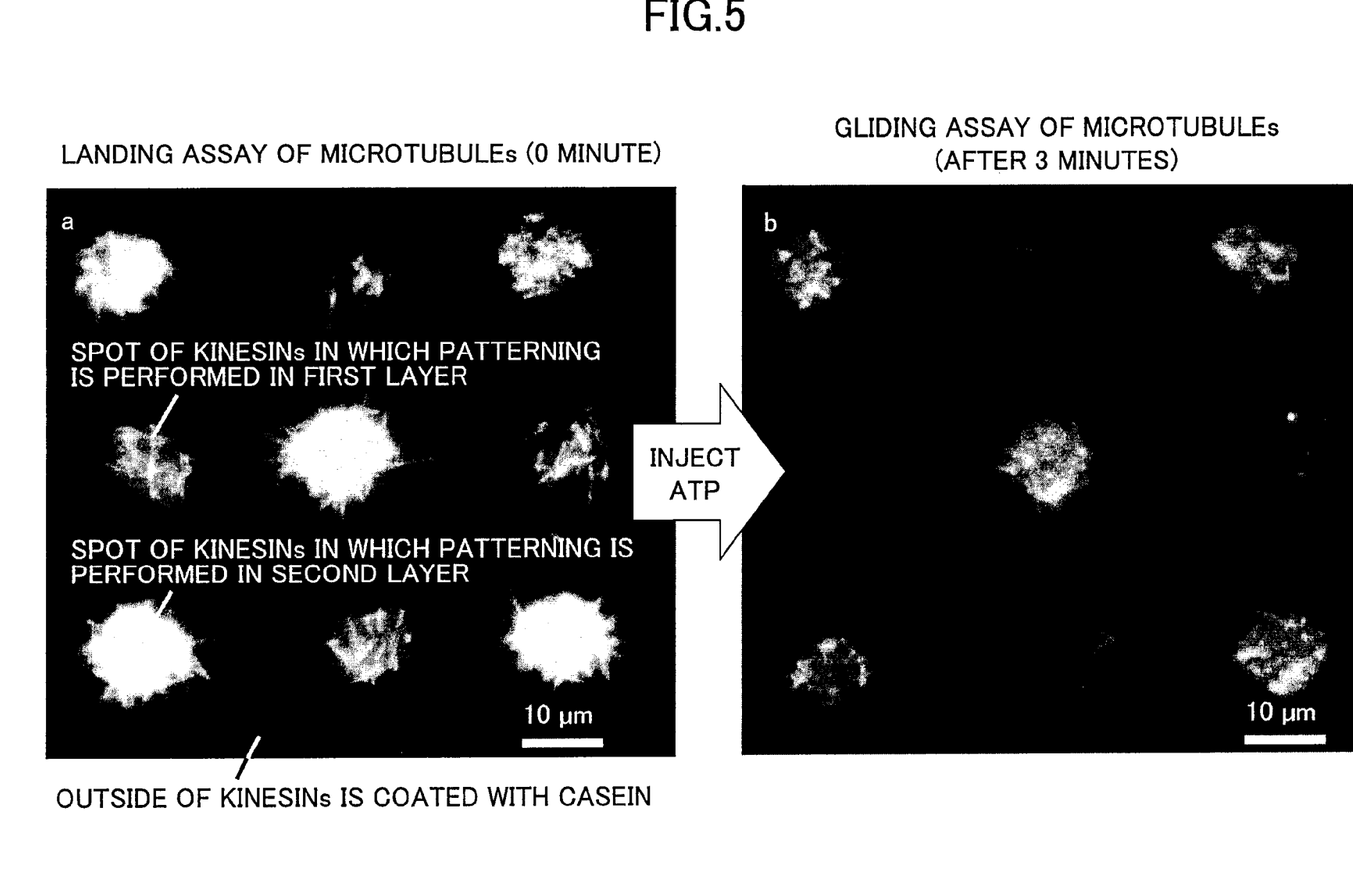
FIG. 5 is an observation image of a fluorescence microscope showing a result of verifying activity of freeze-dried kinesins which are motor proteins.

FIG. 5 is an image of observation of a fluorescence microscope showing a result of an experiment for verifying whether the micro-arrayed proteins of the embodiment of the present invention keeps the functionality.

In this experiment, kinesin which is a motor protein was used as an example of a functional protein. That is, biotinylated BSA of 4 mg/mL, casein of 5 mg/mL, streptavidin of 1 mg/mL labeled with fluorochrome TMR, and biotinylated kinesin of 100 μg/mL were laminated sequentially as the first and the second soft materials, so that a microarray of the kinesin was fabricated by peeling off the poly(para-xylylene) resin. Then, the surface of the glass substrate excluding the spots of the kinesin was coated with casein of 5 mg/mL so that non-specific adsorption was suppressed. When microtubules labeled with the fluorochrome TMR were injected, the microtubules specifically landed only in the spot where the kinesin was fixed, so that a microarray of the microtubules was formed (FIG. 5a).

Next, when a buffer solution including ATP (adenosine triphosphoric acid) was injected, gliding motion of the microtubules landed on the kinesin started. When the microtubules slided outside the spot, binding with the kinesin disappeared, and a phenomenon was confirmed that the microtubules were floating in the solution and were out of the focal spot of the microscope, so that the microtubules were not observed (FIG. 5b).

FIG. 5 shows that the soft material (kinesin) obtained by performing freeze-dry processing in the fabrication process in the embodiment of the present invention keeps the ability to bind with the microtubule and has activity for causing the microtubule to perform sliding movement on the glass substrate.

As described above, it is understood that the microarray fabrication method of the embodiment of the present invention can be applied to DNAs and proteins. But, the embodiment of the present invention is not limited to DNAs and proteins. The present invention can be applied to any soft materials, as long as they can be micro-arrayed, such as RNAs (ribonucleic acids), lipids, microbeads and the like.

Further, although the fabrication method of the embodiment of the present invention includes a process of freeze-drying the soft materials, this does not exclude application of the embodiment of the present invention to a soft material that is hard to be freeze-dried. For example, there is a soft material, such as a liposome that is a lipid bimolecular membrane capsule or a cell, for example, that is unsuitable for freeze-dry among soft materials. But, by chemically-modifying the surface of the material with a single-stranded DNA, biotin, antibody and the like, it is possible to fabricate a microarray. Methods for DNA-modifying the surface of the liposome or cell are disclosed in the following reference documents 1 and 2, a method of biotinylated modification is disclosed in the reference document 3, and a method of antibody-modifying is disclosed in the reference document 4. That is, by fabricating a microarray of the single-stranded DNAs or proteins beforehand using the microarray fabrication method of the embodiment of the present invention, the liposome or the cell can be specifically micro-arrayed even after peeling off the poly(para-xylylene) resin by using DNA hybridization, biotin-avidin binding, antigen-antibody binding, and the like.

REFERENCE DOCUMENTS

1 S. Hiyama, et al., "Biomolecular-motor-based autonomous delivery of lipid vesicles as nano- or microscale reactors on a chip," Lab on a Chip, vol. 10, pp. 2741-2748, 2010.

2 S. C. Hsiao, et al., "Direct cell surface modification with DNA for the capture of primary cells and the investigation of myotube formation on defined patterns," Langmuir, vol. 25, pp. 6985-6991, 2009.

3 D. Stamou, et al., "Self-assembled microarrays of attoliter molecular vessels," Angewandte Chemie International Edition, vol. 42, pp. 5580-5583, 2003.

4 A. Ito, et al., "Magnetite nanoparticle-loaded anti-HER2 immuno-liposomes for combination of antibody therapy with hyperthermia," Cancer Letters, vol. 212, pp. 167-175, 2004.

The present international application claims priority based on Japanese patent application No. 2011-070934, filed in the JPO on Mar. 28, 2011, and the entire contents of the Japanese patent application No. 2011-070934 are incorporated herein by reference.

The invention claimed is:

1. A method for fabricating a microarray of plural kinds of soft materials, the method comprising:
   vapor-depositing a poly(para-xylylene) resin of a first layer on a substrate;
   forming a first micro pattern in the poly(para-xylylene) resin;
   forming a first microarray on a surface of the substrate by pouring a solution of a first soft material;
   freeze-drying the first soft material so as to form a micro-arrayed substrate of the first soft material;
   vapor-depositing and laminating a poly(para-xylylene) resin of a second layer on the micro-arrayed substrate of the first soft material that is freeze-dried;
   forming a second micro pattern in a place different from the first micro pattern on the micro-arrayed substrate of the first soft material by penetrating the poly(para-xylylene) resin of the first layer and the second layer;
   forming a second microarray on a surface of the substrate by pouring a solution of a second soft material; and
   peeling off the poly(para-xylylene) resin of the first layer and the second layer at the same time so as to form a micro-arrayed substrate of the first soft material that is freeze-dried and the second soft material.

2. The method as claimed in claim 1, further comprising:
   freeze-drying the second soft material so as to form a micro-arrayed substrate of the first soft material that is freeze dried and the second soft material that is freeze dried; and then
   vapor-depositing a poly(para-xylylene) resin of a third layer on the micro-arrayed substrate of the first soft material that is freeze-dried and the second soft material that is freeze-dried so as to form a third micro pattern;
   pouring a solution including a third soft material;
   peeling off the poly(para-xylylene) resin of the third layer so as to form a micro-arrayed substrate of the first soft material that is freeze-dried, the second soft material that is freeze-dried, and the third soft material on the same substrate; and
   dissolving the first and the second soft materials by pouring a buffer solution to the micro-arrayed substrate of the first soft material that is freeze-dried, the second soft material that is freeze-dried, and the third soft material.

3. The method for fabricating a microarray of plural kinds of soft materials as claimed in claim 1, further comprising:
   after forming a last microarray on the surface of the substrate by pouring a last solution including a last soft material, freeze-drying the whole substrate on which all of the soft materials are formed in order to preserve the substrate at room temperature or at low temperature until use of the substrate.

4. The method as claimed in claim 1, further comprising, after peeling off the poly(para-xylylene) resin of the first layer and the second layer:
dissolving the first soft material by pouring a buffer solution to the micro-arrayed substrate of the first soft material that is freeze-dried and the second soft material.

5. A method for fabricating a microarray of plural kinds of soft materials, the method comprising:
vapor-depositing a poly(para-xylylene) resin of a first layer on a substrate;
forming a first micro pattern in the poly(para-xylylene) resin;
forming a first microarray on a surface of the substrate by pouring a solution of a first soft material;
peeling off the poly(para-xylylene) resin of the first layer from the substrate on which the first microarray is formed;
freeze-drying the first soft material so as to form a micro-arrayed substrate of the first soft material;
vapor-depositing and laminating a poly(para-xylylene) resin of a second layer on the micro-arrayed substrate of the first soft material that is freeze-dried;
forming a second micro pattern in a place different from the first micro pattern in the poly(para-xylylene) resin of the second layer;
forming a second microarray on the surface of the substrate by pouring a solution of a second soft material; and
peeling off the poly(para-xylylene) resin of the second layer so as to form a micro-arrayed substrate of the first soft material that is freeze-dried and the second soft material.

6. The method as claimed in claim 5, further comprising:
freeze-drying the second soft material so as to form a micro-arrayed substrate of the first soft material that is freeze dried and the second soft material that is freeze dried; and then
vapor-depositing a poly(para-xylylene) resin of a third layer on the micro-arrayed substrate of the first soft material that is freeze-dried and the second soft material that is freeze-dried so as to form a third micro pattern;
pouring a solution including a third soft material;
peeling off the poly(para-xylylene) resin of the third layer so as to form a micro-arrayed substrate of the first soft material that is freeze-dried, the second soft material that is freeze-dried, and the third soft material on the same substrate; and
dissolving the first and the second soft materials by pouring a buffer solution to the micro-arrayed substrate of the first soft material that is freeze-dried, the second soft material that is freeze-dried, and the third soft material.

7. The method for fabricating a microarray of plural kinds of soft materials as claimed in claim 5, further comprising:
after forming a last microarray on the surface of the substrate by pouring a solution including a last soft material, freeze-drying the whole substrate on which all of the soft materials are formed in order to preserve the substrate at room temperature or at low temperature until use of the substrate.

8. The method as claimed in claim 5, further comprising, after peeling off the poly(para-xylylene) resin of the second layer:
dissolving the first soft material by pouring a buffer solution to the micro-arrayed substrate of the first soft material that is freeze-dried and the second soft material.

9. A method for fabricating a microarray of plural kinds of soft materials, the method comprising:
vapor-depositing a poly(para-xylylene) resin of a first layer on a substrate;
forming a first micro pattern in the poly(para-xylylene) resin;
forming a first microarray on a surface of the substrate by pouring a solution of a first soft material;
freeze-drying the first soft material so as to form a micro-arrayed substrate of the first soft material;
peeling off the poly(para-xylylene) resin of the first layer from the substrate on which the first microarray is formed;
vapor-depositing and laminating a poly(para-xylylene) resin of a second layer on the micro-arrayed substrate of the first soft material that is freeze-dried;
forming a second micro pattern in a place different from the first micro pattern in the poly(para-xylylene) resin of the second layer;
forming a second microarray on the surface of the substrate by pouring a solution of a second soft material; and
peeling off the poly(para-xylylene) resin of the second layer so as to form a micro-arrayed substrate of the first soft material that is freeze-dried and the second soft material.

10. The method as claimed in claim 9, further comprising:
freeze-drying the second soft material so as to form a micro-arrayed substrate of the first soft material that is freeze dried and the second soft material that is freeze dried; and then
vapor-depositing a poly(para-xylylene) resin of a third layer on the micro-arrayed substrate of the first soft material that is freeze-dried and the second soft material that is freeze-dried so as to form a third micro pattern;
pouring a solution including a third soft material;
peeling off the poly(para-xylylene) resin of the third layer so as to form a micro-arrayed substrate of the first soft material that is freeze-dried, the second soft material that is freeze-dried, and the third soft material on the same substrate; and
dissolving the first and the second soft materials by pouring a buffer solution to the micro-arrayed substrate of the first soft material that is freeze-dried, the second soft material that is freeze-dried, and the third soft material.

11. The method for fabricating a microarray of plural kinds of soft materials as claimed in claim 9, further comprising:
after forming a last microarray on the surface of the substrate by pouring a solution including a last soft material, freeze-drying the whole substrate on which all of the soft materials are formed in order to preserve the substrate at room temperature or at low temperature until use of the substrate.

12. The method as claimed in claim 9, further comprising, after peeling off the poly(para-xylylene) resin of the second layer:
dissolving the first soft material by pouring a buffer solution to the micro-arrayed substrate of the first soft material that is freeze-dried and the second soft material.

* * * * *